US011304589B2

(12) United States Patent
Tanaka

(10) Patent No.: US 11,304,589 B2
(45) Date of Patent: Apr. 19, 2022

(54) ENDOSCOPE AND ENDOSCOPE SYSTEM

(71) Applicant: OLYMPUS CORPORATION, Tokyo (JP)

(72) Inventor: Takanori Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 94 days.

(21) Appl. No.: 16/826,825

(22) Filed: Mar. 23, 2020

(65) Prior Publication Data

US 2020/0214540 A1 Jul. 9, 2020

Related U.S. Application Data

(63) Continuation of application No. PCT/JP2018/018907, filed on May 16, 2018.

(30) Foreign Application Priority Data

Sep. 29, 2017 (JP) .............................. JP2017-190429

(51) Int. Cl.
*A61B 1/00* (2006.01)
*H04N 5/217* (2011.01)
*A61B 1/05* (2006.01)

(52) U.S. Cl.
CPC ...... *A61B 1/00009* (2013.01); *A61B 1/00006* (2013.01); *A61B 1/051* (2013.01); *H04N 5/217* (2013.01)

(58) Field of Classification Search
CPC . A61B 1/00006; A61B 1/00009; A61B 1/045; H04J 3/00; H04N 2005/2255; H04N 5/23227; H04N 5/378
See application file for complete search history.

(56) References Cited

U.S. PATENT DOCUMENTS

2009/0213212 A1* 8/2009 Nakamura ......... A61B 1/00006
348/65
2009/0216080 A1* 8/2009 Nakamura ........... H04N 5/3765
600/109
(Continued)

FOREIGN PATENT DOCUMENTS

JP  2008-131391 A  6/2008
JP  2012-010160 A  1/2012

OTHER PUBLICATIONS

"Design of the Linear Array CCD Acquisition System that Line Frequency and Integration Time Adjustable"—Tao Hu, Ya-nan Chen; 2011 International Conference on Electronics and Optoelectronics (ICEOE 2011) (Year: 2011).*
(Continued)

*Primary Examiner* — Mainul Hasan
(74) *Attorney, Agent, or Firm* — Scully, Scott, Murphy & Presser, P.C.

(57) ABSTRACT

An endoscope includes: an imager; a transmission path configured to connect a controller and the imager with each other; a superimposed signal generating circuit configured to generate, as a superimposed signal, a signal obtained by associating High and Low of a pulsed data signal with a change in a pulse width of a pulsed reference clock signal; a parallel-serial converter circuit configured to perform parallel-serial conversion on the imaging signal; a PLL circuit configured to generate a multiplied clock signal; a restoring circuit configured to restore, based on the superimposed signal and the multiplied clock signal, the reference clock signal and the data signal contained in the superimposed signal; and a timing generating circuit configured to generate, based on the reference clock signal and the data signal, a drive signal for driving the imager.

9 Claims, 9 Drawing Sheets

(56) References Cited

U.S. PATENT DOCUMENTS

| | | | | |
|---|---|---|---|---|
| 2011/0292194 | A1* | 12/2011 | Kato ..................... | A61B 1/045 |
| | | | | 348/65 |
| 2011/0298908 | A1* | 12/2011 | Murakami ......... | A61B 1/00009 |
| | | | | 348/65 |
| 2012/0178992 | A1* | 7/2012 | Fujimoto ............... | H04N 7/183 |
| | | | | 600/109 |
| 2012/0320176 | A1* | 12/2012 | Tanaka ............... | A61B 1/00016 |
| | | | | 348/65 |
| 2013/0271586 | A1* | 10/2013 | Komine ................ | A61B 1/045 |
| | | | | 348/65 |
| 2014/0092216 | A1* | 4/2014 | Kawata ................. | H04N 5/378 |
| | | | | 348/45 |
| 2014/0176691 | A1* | 6/2014 | Minakuchi ............ | H04N 7/183 |
| | | | | 348/65 |

OTHER PUBLICATIONS

"A 3.0 GB/s Clock Data Recovery Circuits Based on Digital DLL for Clock-Embedded Display Interface"—Jae-Wook Kwon, Xuefan Jin, Gyoo-Cheol Hwang, Jung-Hoon Chun and Kee-Won Kwon; 978-1-4673-2213-3/12/$31.00 © 2012 IEEE (Year: 2012).*
International Search Report dated Jun. 26, 2018 issued in PCT/JP2018/018907.
Design Wave Magazine, Jan. 2004, pp. 60-61, non-official translation (Kakesu, Toshio, Basics of design is understanding of specifications—Minimum knowledge to know for realizing high-speed serial communication), with partial translation, cited in ISR.

* cited by examiner

L

H

ENDOSCOPE AND ENDOSCOPE SYSTEM

CROSS-REFERENCE TO RELATED APPLICATION

This application is a continuation of PCT International Application No. PCT/JP2018/018907 filed on May 16, 2018, which designates the United States, incorporated herein by reference, and which claims the benefit of priority from Japanese Patent Application No. 2017-190429, filed on Sep. 29, 2017, incorporated herein by reference.

BACKGROUND

1. Technical Field

The present disclosure relates to an endoscope configured to capture an image of a subject and generate image data on the subject and to an endoscope system.

2. Related Art

In the related art, an analog imaging signal is transmitted from an imager that is arranged in a distal end part of an insertion portion to be inserted into a subject to a processor device that is connected to a scope proximal end part and, after given image processing is performed, the resultant image is displayed on a display monitor. The diameter of the distal end part of the insertion portion is reduced in order to reduce the stress applied on the subject when the insertion portion is inserted. For this reason, a drive circuit for driving the imager and a device for processing the imaging signal are arranged on a scope board or a processor device and a drive signal is transmitted from a side of a processor device to the imager at the distal end part via a signal line passing through a universal cord.

A recent increase in functionality of endoscopes involves a need for transmission of various control signals other than drive signals from the processor device to the distal end part and therefore a technique of reducing the diameter of the distal end part by superimposing multiple signals and thus reducing the number of signal lines has been known (refer to Japanese Laid-open Patent Publication No. 2012-10160). According to the technique, a PLL circuit is arranged in the distal end part, a transmission signal in which the period of one of a rise edge and a falling edge of a pulse signal matches that of a reference clock signal and the position of the other edge is modulated in accordance with serial data is transmitted to the distal end part via a transmission path, the PLL circuit multiplies the transmission signal by 1 and thus reproduces a reference clock signal from which jitters are removed and reproduces serial data based on the reference signal.

SUMMARY

In some embodiments, an endoscope includes: an imager configured to generate an imaging signal by receiving light and performing photoelectric conversion; a transmission path configured to connect a controller configured to perform image processing on the imaging signal that is generated by the imager, and the imager with each other and transmit the imaging signal; a superimposed signal generating circuit that is arranged on a side of a proximal end of the transmission path, the superimposed signal generating circuit being configured to generate, as a superimposed signal, a signal obtained by associating High and Low of a pulsed data signal that is input from an outside with a change in a pulse width of a pulsed reference clock signal that is input from an outside and output the superimposed signal to the transmission path; a parallel-serial converter circuit that is arranged on a side of a distal end of the transmission path, the parallel-serial converter circuit being configured to perform parallel-serial conversion on the imaging signal and output the converted imaging signal to the transmission path; a PLL circuit that is arranged on the side of the distal end of the transmission path, the PLL circuit being configured to generate a multiplied clock signal that is obtained by multiplying a frequency of the superimposed signal by at least 2 in synchronization with any one of a rise edge and a falling edge of the superimposed signal, the multiplied clock signal being a signal for driving the parallel-serial converter circuit; a restoring circuit that is arranged on the side of the distal end of the transmission path, the restoring circuit being configured to restore, based on the superimposed signal and the multiplied clock signal, the reference clock signal and the data signal contained in the superimposed signal; and a timing generating circuit that is arranged on the side of the distal end of the transmission path, the timing generating circuit being configured to generate, based on the reference clock signal and the data signal, a drive signal for driving the imager.

In some embodiments, an endoscope system includes: an endoscope including an imager configured to generate an imaging signal by receiving light and performing photoelectric conversion; a controller configured to perform image processing on the imaging signal that is generated by the imager; a transmission path configured to connect the imager and the controller with each other and transmit the imaging signal; a data signal generating circuit configured to generate a pulsed data signal and output the pulsed data signal; a reference clock signal generating circuit configured to generate a pulsed reference clock signal and output the pulsed reference clock signal; a superimposed signal generating circuit that is arranged on a side of a proximal end of the transmission path, the superimposed signal generating circuit being configured to generate, as a superimposed signal, a signal obtained by associating High and Low of the data signal with a change in a pulse width of the reference clock signal and output the superimposed signal to the transmission path; a parallel-serial converter circuit that is arranged on a side of a distal end of the transmission path, the parallel-serial converter circuit being configured to perform parallel-serial conversion on the imaging signal and then output the converted imaging signal to the transmission path; a PLL circuit that is arranged on the side of the distal end of the transmission path, the PLL circuit being configured to generate a multiplied clock signal that is obtained by multiplying a frequency of the superimposed signal by at least 2 in synchronization with any one of a rise edge and a falling edge of the superimposed signal, the multiplied clock signal being a signal for driving the parallel-serial converter circuit; a restoring circuit that is arranged on the side of the distal end of the transmission path, the restoring circuit being configured to restore, based on the superimposed signal and the multiplied clock signal, the reference clock signal and the data signal contained in the superimposed signal; and a timing generating circuit that is arranged on the side of the distal end of the transmission path, the timing generating circuit being configured to generate, based on the reference clock signal and the data signal, a drive signal for driving the imager.

The above and other features, advantages and technical and industrial significance of this disclosure will be better

DETAILED DESCRIPTION

Modes for carrying out the disclosure ("embodiments below") will be described in detail below with reference to the accompanying drawings. Note that the following embodiments do not limit the disclosure. Each drawing referred to in the following description only schematically illustrates shapes, sizes and positional relationships to an extent such that the content of the disclosure can be understood. In other words, the disclosure is not limited to the shapes, sizes, and positional relationships exemplified in each drawing. In the following description, an endoscope system including a flexible endoscope will be descried as an exemplary endoscope system.

First Embodiment

Configuration of Endoscope System

Figure 1:
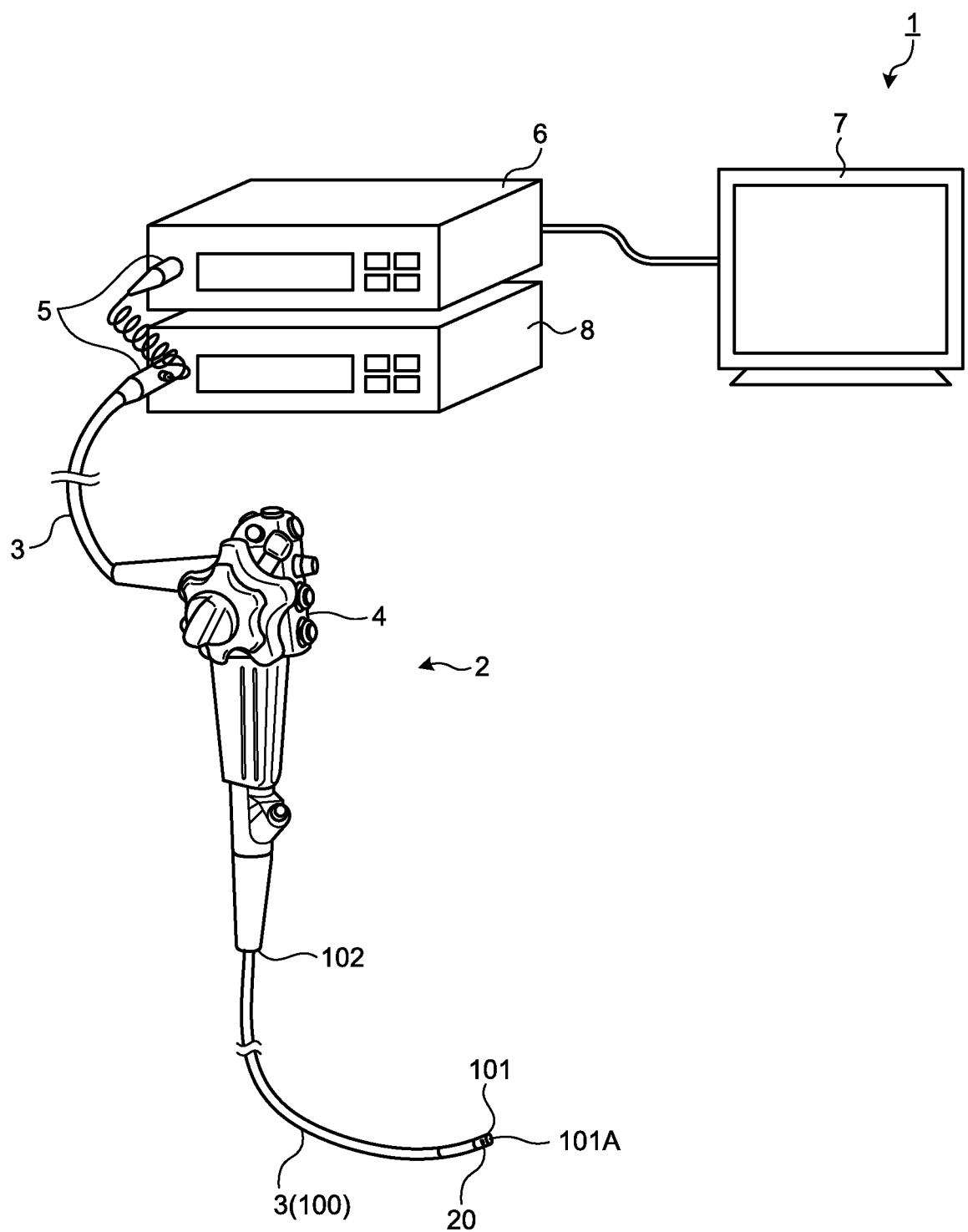
FIG. 1 is a schematic diagram schematically illustrating am entire configuration of an endoscope system according to a first embodiment of the disclosure.

FIG. 1 is a schematic diagram schematically illustrating an entire configuration of an endoscope system according to the first embodiment of the disclosure. An endoscope system 1 illustrated in FIG. 1 includes an endoscope 2, a processor 6 (controller), a display device 7, and a light source device 8.

The endoscope 2 includes a transmission cable 3, an operation unit 4, and a connector 5. An insertion portion 100 of the endoscope 2 is inserted into a body cavity of a subject and the endoscope 2 capture in-vivo images of the subject, generates imaging signals, and outputs the imaging signal to the processor 6. In the endoscope 2, an imaging unit 20 that captures in-vivo images of the subject and generate imaging signals is arranged on a side of a distal end part 101 of the insertion portion 100 that is inserted into the body cavity of the subject, which is the side of one end of the transmission cable 3, and the operation unit 4 that receives various operations on the endoscope 2 is connected to a side of a proximal end 102 of the insertion portion 100. The imaging signals that are generated by the imaging unit 20 are output to the connector 5 via the transmission cable 3 having a length of at least 10 cm. The connector 5 is detachably connected to the processor 6 and the light source device 8, performs given image processing on the imaging signals that are output by the imaging unit 20, and outputs the processed imaging signals to the processor 6. The imaging unit 20 is arranged in parallel with an opening face 101A of the distal end part 101 of the endoscope 2.

The processor 6 performs given image processing on the imaging signals that are input from the connector 5, outputs the processed imaging signals to the display device 7, and comprehensively controls the entire endoscope system 1.

Under the control of the processor 6, the display device 7 displays an image corresponding to the imaging signals that are input from the processor 6. The display device 7 is formed using organic electro luminescence (EL) or liquid crystals.

The light source device 8 is formed using, for example, a halogen lamp or a white light emitting diode (LED) and applies illumination light to the subject from the side of the distal end part 101 of the insertion portion 100 of the endoscope 2 via the connector 5 and the transmission cable 3.

Functional Configuration of Relevant Part of Endoscope System

Figure 2:
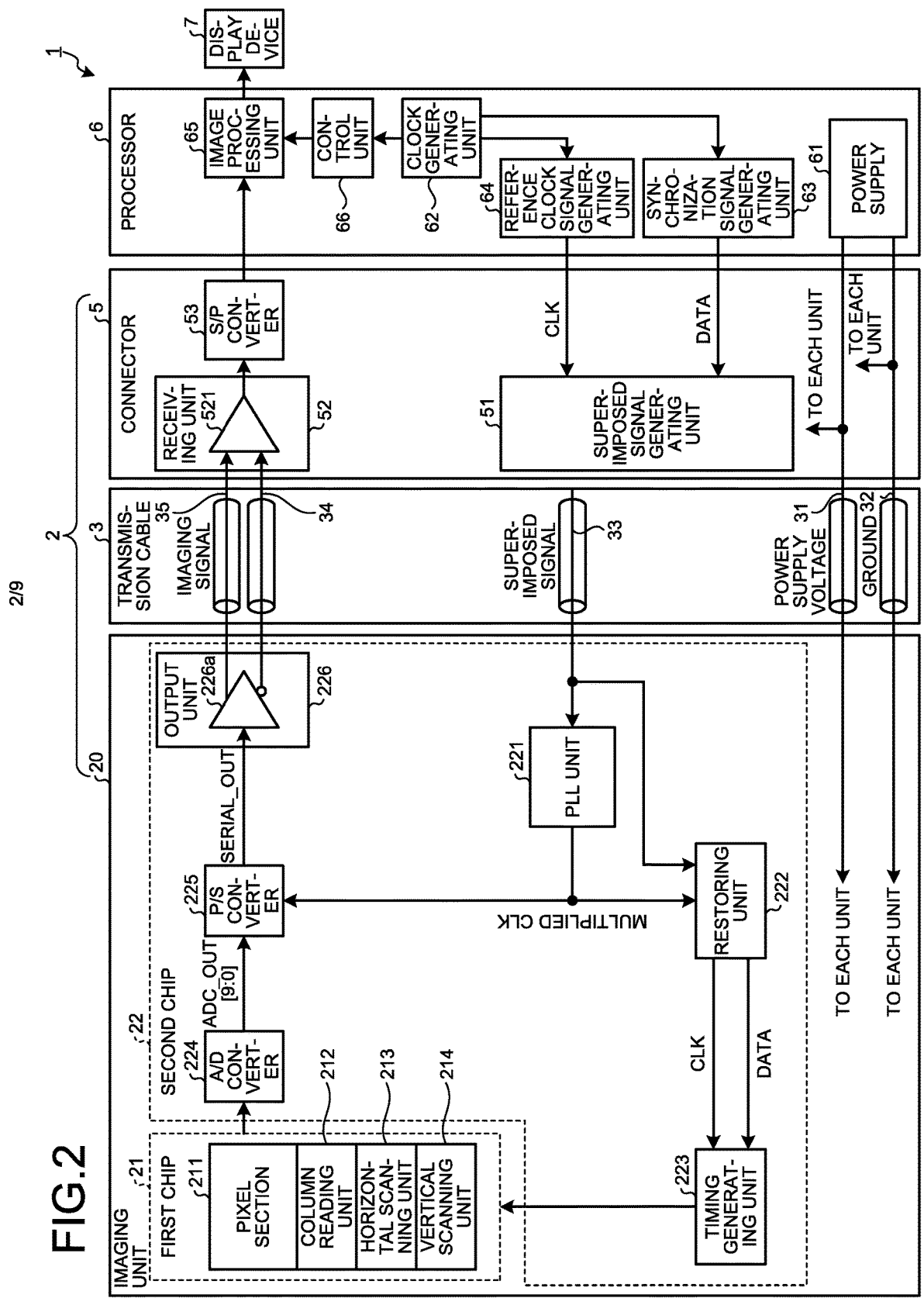
FIG. 2 is a block diagram illustrating a functional configuration of a relevant part of the endoscope system according to the first embodiment of the disclosure.

A functional configuration of a relevant part of the above-described endoscope system 1 will be described. FIG. 2 is a block diagram illustrating the functional configuration of the relevant part of the endoscope system 1.

Configuration of Endoscope

First of all, the configuration of the endoscope 2 will be described.

As illustrated in FIG. 2, the endoscope 2 includes at least the imaging unit 20, the transmission cable 3, and the connector 5.

Configuration of Imaging Unit

First of all, a configuration of the imaging unit 20 will be described.

As illustrated in FIG. 2, the imaging unit 20 receives light and performs photoelectric conversion, thereby generating an imaging signal. The imaging unit 20 includes at least a first chip 21 and a second chip 22. Each of the first chip 21 and the second chip 22 are semiconductor substrates that are of a laminated semiconductor substrate on which each of a plurality of functional devices to be described below is arranged and whose size in the direction of the horizontal plane is smaller than 1 cm×1 cm.

The first chip 21 includes a pixel section 211 that is formed by arranging a plurality of pixels that are arranged in a two-dimensional matrix, receive light from the outside, generate imaging signals corresponding to the amounts of received light by performing photoelectric conversion, and output the imaging signals; a column reading unit 212 that performs given image processing (for example, correlated double sampling (CDS)) on the imaging signals that are read from the pixel section 211 and outputs the processed imaging signals to an A/D converter 224 to be described below; a vertical scanning unit 214 that sequentially selects rows of pixels of the pixel section 211 one by one and outputs the imaging signals accumulated in the pixels to the column reading unit 212; and a horizontal scanning unit 213 that controls the column reading unit 212 and causes the column reading unit 212 to output the imaging signals of the pixels that are processed by the column reading unit 212 sequentially to the A/D converter 224 one by one. In the first embodiment, the first chip 21 functions as an imager. Arrangement of each functional device on the first chip 21 will be described below.

The second chip 22 includes a PLL unit 221, a restoring unit 222, a timing generating unit 223, the A/D converter 224, a parallel-serial converter 225 ("P/S converter 225" below), and an output unit 226. Arrangement of each functional device on the second chip 22 will be described below.

The PLL unit 221 is arranged on a side of a distal end of a signal line 33 of the transmission cable 3. The PLL unit 221 generates a multiplied clock signal ("multiplied CLK" below) whose frequency is higher than that of the superimposed signal in synchronization with any one of a rise edge and a falling edge of a superimposed signal that is input from a superimposed signal generating unit 51 of the connector 5 and that is for driving the P/S converter 225, and outputs the multiplied clock signal to the restoring unit 222. Specifically, the PLL unit 221 generates a multiplied CLK obtained by multiplying the frequency of the superimposed signal by at least 2 in synchronization with any one of the rise edge and the falling edge of the superimposed signal that is input from the superimposed signal generating unit 51 of the connector 5 and outputs the generated multiplied CLK to the P/S converter 225 and the restoring unit 222. The first embodiment will be described as one where the multiplying number of the PLL unit 221 is 10.

Figure 3:
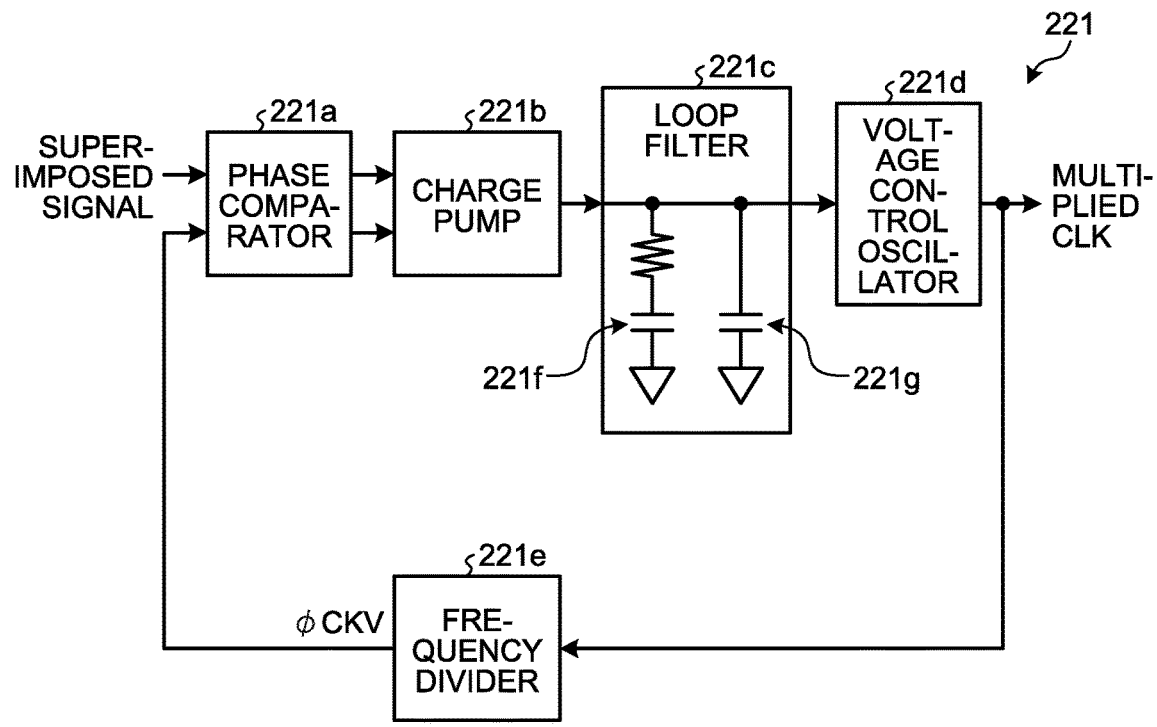
FIG. 3 is a block diagram illustrating a functional configuration of a PLL unit according to the first embodiment of the disclosure.

FIG. 3 is a block diagram of a functional configuration of the PLL unit 221.

As illustrated in FIG. 3, the PLL unit 221 includes a phase comparator 221a, a charge pump 221b, a loop filter 221c, a voltage control oscillator 221d, and a frequency divider 221e.

The phase comparator 221a compares phases of two input signals and outputs a difference between the phases to the charge pump 221b. Specifically, the phase comparator 221a compares the phase of the superimposed signal that is input from the superimposed signal generating unit 51 of the connector 5 via the signal line 33 of the transmission cable 3 and the phase of a signal φCKV obtained by dividing the frequency of the multiplied CLK that is input from the frequency divider 221e and outputs the difference between the phases to the charge pump 221b.

The charge pump 221b outputs a current (or voltage) proportional to the difference that is input from the phase comparator 221a to the loop filter 221c.

The loop filter 221c performs smoothing on the pulse signal that is input from the charge pump 221b and outputs the smoothed pulse signal to the voltage control oscillator 221d. The loop filter 221c includes a lead-lag filter 221f and a low-pass filter 221g that determine loop characteristics.

The voltage control oscillator 221d outputs, to the outside and the frequency divider 221e, the multiplied CLK obtained by multiplying the frequency of the superimposed signal based on the voltage that is input from the loop filter 221c.

The frequency divider 221e outputs, to the phase comparator 221a, the signal φCKV obtained by converting the multiplied CLK that is input from the voltage control oscillator 221d into a pulse signal (obtained by dividing the frequency of the multiplied CLK by an integer larger than than 1).

FIG. 2 will be referred back to continue describing the configuration of the second chip 22.

The restoring unit 222 is arranged on the side of the distal end of the signal line 33 of the transmission cable 3. Based on the superimposed signal that is input from the connector 5 via the signal line 33 of the transmission cable 3 and the multiplied CLK that is input from the PLL unit 221, the restoring unit 222 restores the reference clock signal CLK and a data signal DATA contained in the superimposed signal and outputs the restored reference clock signal CLK and the data signal DATA to the timing generating unit 223.

Figure 4:
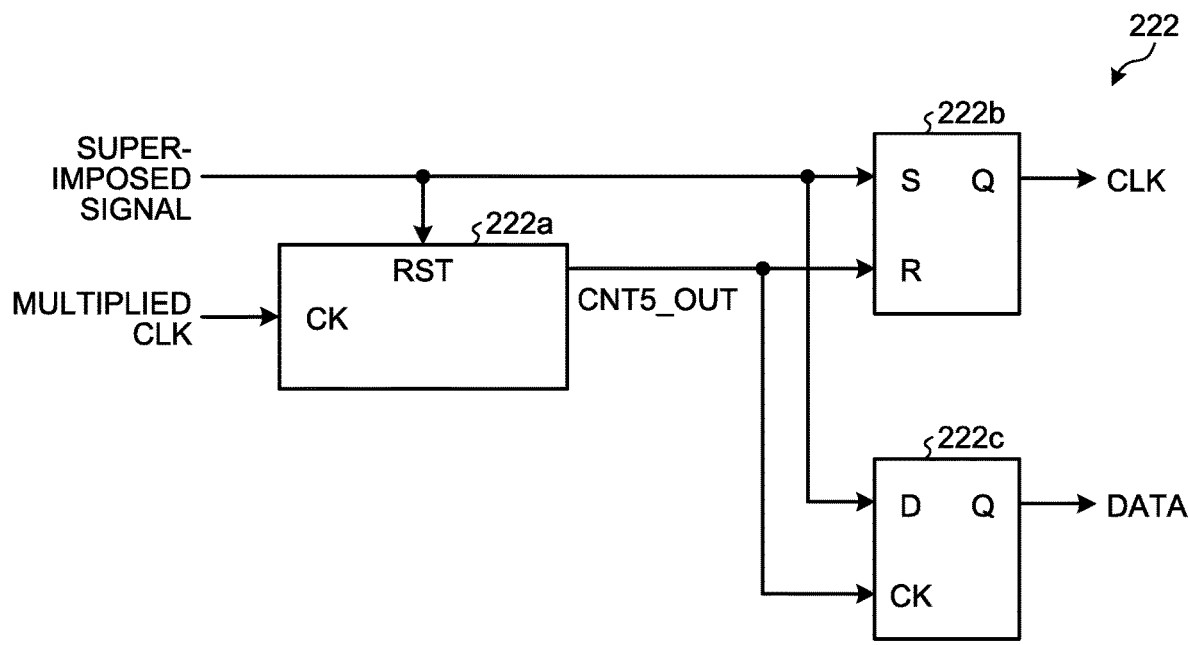
FIG. 4 is a block diagram illustrating a functional configuration of a restoration unit according to the first embodiment of the disclosure.

FIG. 4 is a block diagram illustrating a functional configuration of the restoring unit 222.

As illustrated in FIG. 4, the restoring unit 222 includes a counter unit 222a, a clock restoring unit 222b, and a data restoring unit 222c.

The counter unit 222a is formed using a quinary counter circuit, and the superimposed signal and the multiplied CLK are input to the counter unit 222a. The counter unit 222a counts pulses corresponding to rise edges of the multiplied CLK. Specifically, the counter unit 222a outputs a pulse signal CNT5_OUT corresponding to the fifth rise edge of the multiplied signal CLK to the clock restoring unit 222b and the data restoring unit 222c.

The clock restoring unit 222b is formed using an RS latch circuit, and the superimposed signal and the pulse signal CNT5_OUT that is input from the counter unit 222a are input to the clock restoring unit 222b. The clock restoring unit 222b restores the reference clock signal CLK whose pulse widths are constant and outputs the reference clock signal CLK to the timing generating unit 223. Specifically, the clock restoring unit 222b sets (High) a rise edge of the superimposed signal and, using the rise position of the multiplied signal as a reference, performs resetting (Low) at the fifth rise edge of the multiplied CLK, and thus restores the reference clock signal CLK whose pulse widths are constant and then outputs the reference clock signal CLK to the timing generating unit 223.

The data restoring unit 222c is formed using a D flip-flop circuit. The superimposed signal and the pulse signal CNT5_OUT that is input from the counter unit 222a are input to the data restoring unit 222c. The data restoring unit 222c restores the data signal DATA by converting the length of the pulse width of the superimposed signal to High or Low of a digital signal and outputs the restored data signal DATA to the timing generating unit 223. Specifically, using a rise of the superimposed signal as a reference, the data restoring unit 222c restores the data signal DATA by latching the superimposed signal at the timing of the fifth rise edge of the multiplied CLK and thus converting the length of the pulse width to High or Low of a digital signal and then outputs the restored data signal DATA to the timing generating unit 223.

FIG. 2 will be referred back to continue describing the configuration of the second chip 22.

The timing generating unit 223 generates a drive signal for driving the first chip 21 (imager) based on the reference clock signal CLK and the data signal DATA that are input from the restoring unit 222 and outputs the drive signal to the first chip 21.

The A/D converter 224 generates an digital imaging signal ADC_OUT [9:0] by performing A/D conversion processing on the analog imaging signal that is output from the first chip 21 and outputs the digital imaging signal ADC_OUT [9:0] to the P/S converter 225. In the first embodiment, the number of bits of the digital imaging signal ADC_OUT [9:0] generated by the A/D converter 224 is described as 10 bits; however the number of bits is not limited thereto and the number of bits can be changed as appropriate and even an imaging signal of 12 bits is applicable.

The P/S converter 225 outputs, to the output unit 226, an imaging signal SERIAL_OUT that is serial data into which the digital imaging signal ADC_OUT [9:0] that is input from the A/D converter 224 is converted by performing, based on the multiplied CLK, parallel/serial conversion on the digital imaging signal ADC_OUT [9:0].

The output unit 226 outputs the imaging signal SERIAL_OUT that is input from the P/S converter 225 to the connector 5 by low voltage difference signaling (LVDS) via the two signal lines 34 and 35 of the transmission cable 3. The output unit 226 includes a differential amplifier 226a that outputs the imaging signal SERIAL_OUT that is input from the P/S converter 225 via the two signal lines 34 and 35. In the first embodiment, the output unit 226 outputs the imaging signal SERIAL_OUT, which is input from the P/S converter 225, via the two signal lines 34 and 35 by LVDS. Alternatively, the imaging signal SERIAL_OUT may be output to the connector 5 in a manner that the imaging signal SERIAL_OUT is superimposed onto another signal line and is output or that the imaging signal SERIAL_OUT is output according to another method.

Configuration of Transmission Cable

A configuration of the transmission cable 3 will be described.

The transmission cable 3 is formed using a plurality of signal lines. Specifically, the transmission cable 3 includes at least a signal line 31 that transmits a power supply voltage, a signal line 32 that transmits a ground, the signal line 33 that transmits the superimposed signal, and the signal lines 34 and 35 that transmit the imaging signal by LVDS. In the first embodiment, the transmission cable 3 serves as a transmission path.

Configuration of Connector

A configuration of the connector 5 will be described.

The connector 5 includes the superimposed signal generating unit 51, a receiving unit 52, and a S/P converter 53.

The superimposed signal generating unit 51 is arranged on a side of a proximal end of the transmission cable 3 and generates, as the superimposed signal, a signal obtained by associating High and Low of the data signal DATA, which is input from a synchronization signal generating unit 63 of the processor 6 to be described below, with a change in the pulse width of the reference clock signal CLK, which is input from a reference clock signal generating unit 64 of the processor 6 to be described below, and outputs the superimposed signal to the signal line 33 of the transmission cable 3. Specifically, the superimposed signal generating unit 51 generates, as the superimposed signal, a signal obtained by converting High and Low of the data signal DATA to the length of the pulse width of the reference clock signal CLK and outputs the superimposed signal to the signal line 33 of the transmission cable 3.

The receiving unit 52 receives the imaging signal that is transmitted by LVDS via the signal lines 34 and 35 of the transmission cables 3 and outputs the imaging signal to the S/P converter 53. The receiving unit 52 includes a receiving amplifier 521 that receives the imaging signal that is transmitted by LVDS via the signal lines 34 and 35 of the transmission cable 3.

The S/P converter 53 performs serial/parallel conversion on the imaging signal that is input from the receiving unit 52 and outputs the resultant imaging signal to an image processing unit 65 of the processor 6 to be described below.

Configuration of Processor

A configuration of the processor 6 will be described.

The processor 6 includes a power supply 61, a clock generating unit 62, a synchronization signal generating unit 63, the reference clock signal generating unit 64, the image processing unit 65, and a control unit 66.

The power supply 61 generates a power supply voltage (VDD) and outputs the generated power supply voltage and a ground (GND) to the imaging unit 20 and the connector 5 via the signal line 31 and the signal line 32 of the transmission cable 3.

The clock generating unit 62 generates a clock signal serving as a reference of operations of each component of the endoscope system 1 and outputs the clock signal to the synchronization signal generating unit 63, the reference clock signal generating unit 64, and the control unit 66. The clock generating unit 62 is formed using a clock module.

The synchronization signal generating unit 63 generates the pulsed data signal DATA based on the clock signal that is input from the clock generating unit 62 and outputs the pulsed data signal DATA to the superimposed signal generating unit 51 of the connector 5. The data signal DATA contains the synchronization signal (HSYNC or the like) and a control signal to the imaging unit 20. In the first embodiment, the synchronization signal generating unit 63 functions as a data signal generating unit.

The reference clock signal generating unit 64 generates the pulsed reference clock signal CLK based on the clock signal that is input from the clock generating unit 62 and outputs the data signal DATA to the clock generating unit 62 and outputs the reference clock signal CLK to the superimposed signal generating unit 51 of the connector 5.

The image processing unit 65 performs given image processing on the imaging signal that is input from the S/P converter 5 of the connector 5 and outputs the processed imaging signal to the display device 7. The given image processing is, for example, white balance adjustment processing and demosaicing processing.

The control unit 66 comprehensively controls each unit of the endoscope system 1. The control unit 66 is formed using, a central processing unit (CPU), etc.

Arrangement of Each Chip

Arrangement of each functional device of the first chip 21 and the second chip 22 described above will be described.

Figure 5:
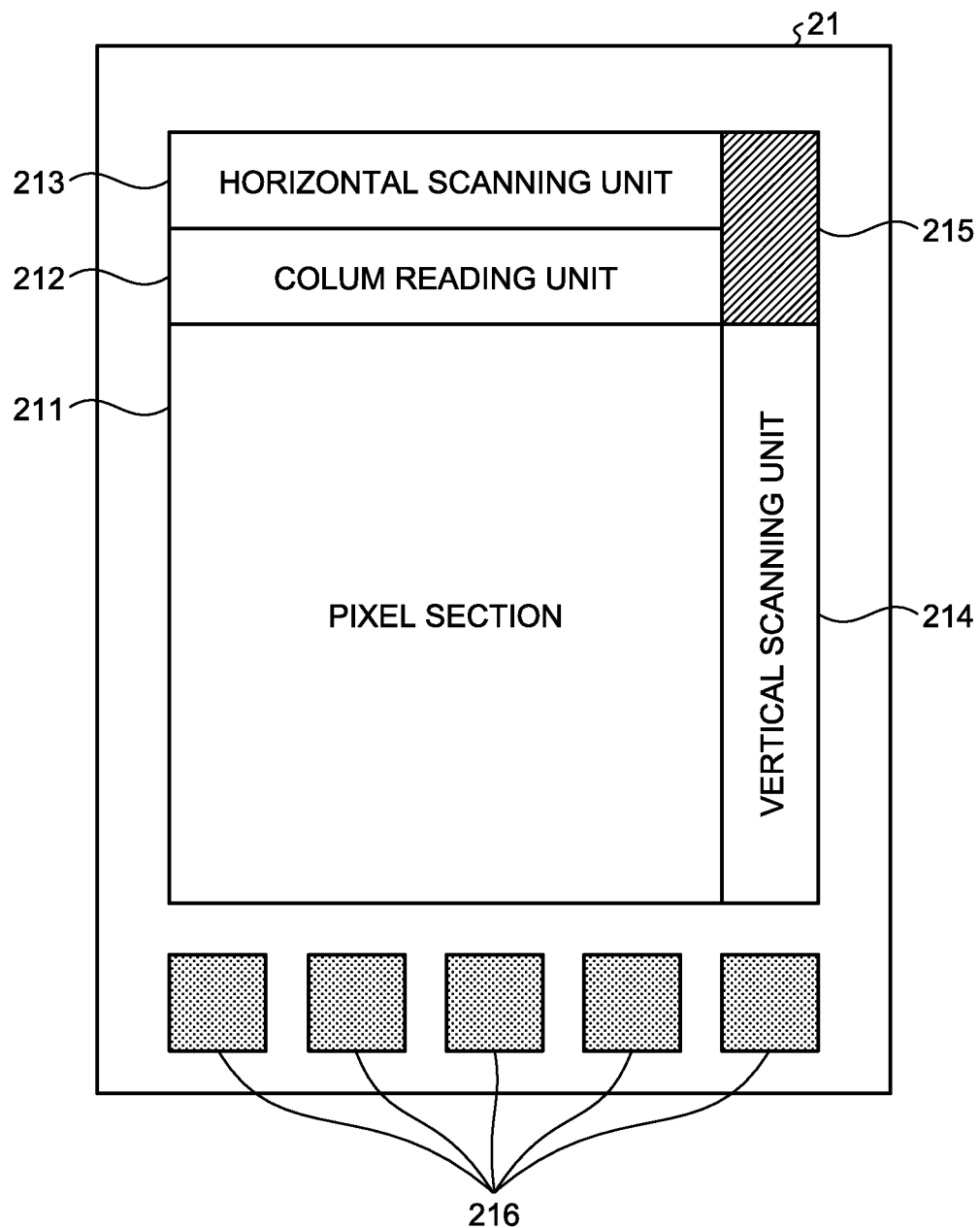
FIG. 5 is a plane view schematically illustrating exemplary arrangement of functional devices of a first chip according to the first embodiment of the disclosure.
Figure 6:
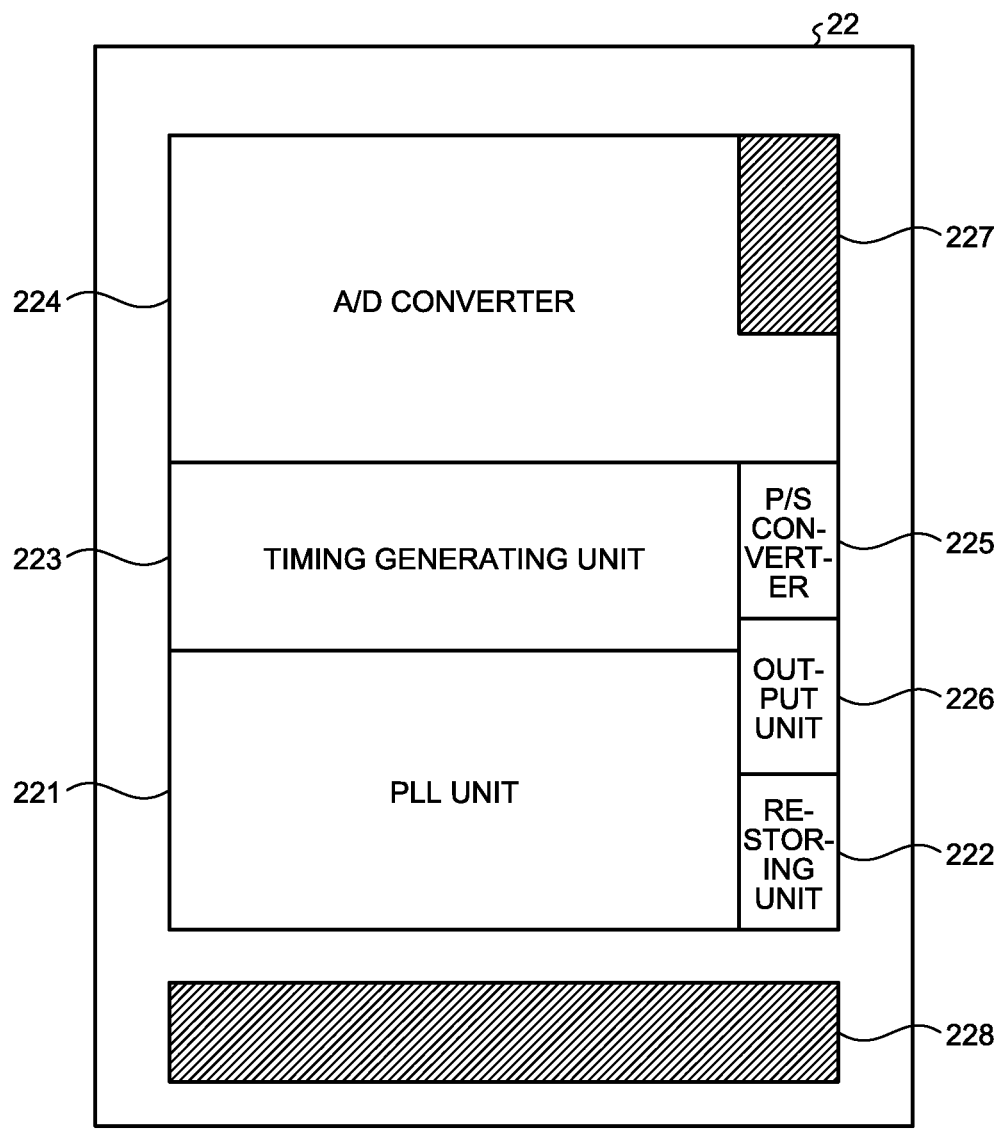
FIG. 6 is a plane view schematically illustrating exemplary arrangement of functional devices of a second chip according to the first embodiment of the disclosure.

FIG. 5 is a plane view schematically illustrating exemplary arrangement of functional devices of the first chip 21. FIG. 6 is a plane view schematically illustrating exemplary arrangement of functional devices of the second chip 22.

As illustrated in FIG. 5, the first chip 21 includes a connector 215 and a plurality of electrode pads 216 in addition to the pixel section 211, the column reading unit 212, the horizontal scanning unit 213, and the vertical scanning unit 214.

The connector 215 is formed using a through silicon via (TSV). The connector 215 electrically connects the first chip 21 and the second chip 22 with each other and transmits control signals respectively for the pixel section 211, the column reading unit 212, the horizontal scanning unit 213, and the vertical scanning unit 214 from the second chip 22 to the first chip 21 and transmits the imaging signal from the first chip 21 to the second chip 22.

The signal lines 31 to 35 of the transmission cable 3 are connected respectively to the electrode pads 216 and the electrode pads 216 transmit the power supply voltage, the ground, the superimposed signal, and the imaging signal to the second chip 22.

As illustrated in FIG. 6, the second chip 22 includes a connector 227 and a connector 228 in addition to the PLL unit 221, the restoring unit 222, the timing generating unit 223, the A/D converter 224, the P/S converter 225, and the output unit 226 that are described above.

The connector 227 electrically connects the first chip 21 and the second chip 22 with each other and transmits control signals respectively for the pixel section 211, the column reading unit 212, the horizontal scanning unit 213 and the vertical scanning unit 214 from the second chip 22 to the first chip 21 and transmits the imaging signal from the first chip 21 to the second chip 22.

The connector 228 transmits, to the second chip 22, the power supply voltage, the ground, the superimposed signal and the imaging signal that are transmitted via the electrode pads 216 on the first chip 21.

The imaging unit 20 configured as described above is formed by superimposing the first chip 21 on the second chip 22. The arrangement of each functional device in FIG. 5 and FIG. 6 is an example only and the arrangement may be changed as appropriate. For example, the functional devices of the first chip 21 excluding the pixel section 211 may be arranged on the second chip 22 and, when the imaging unit 20 is formed by back surface irradiation, the second chip 22 may be superimposed on the first chip 21.

Operations of Endoscope System

Operations of each unit of the endoscope system 1 will be described.

Figure 7:
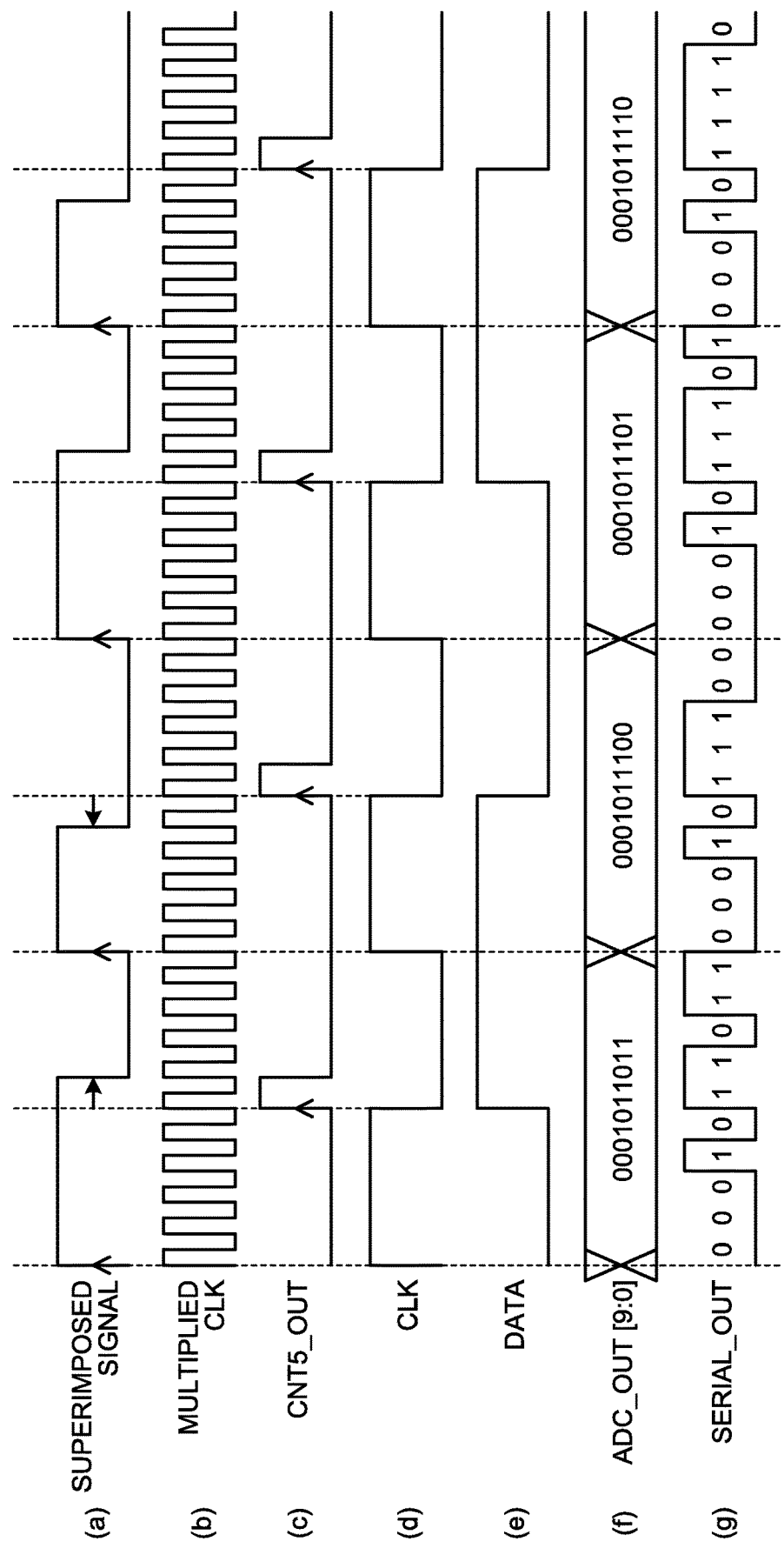
FIG. 7 is a diagram schematically illustrating a timing chart of operations of each unit of the endoscope system according to the first embodiment of the disclosure.

FIG. 7 is a diagram schematically illustrating a timing chart of operations of each unit of the endoscope system 1. In FIG. 7, from the top, (a) represents the superimposed signal, (b) represents the multiplied CLK, (c) represents the pulse signal CNT5_OUT, (d) represents the reference clock signal CLK, (e) represents the data signal DATA, (f) represents the digital imaging signal ADC_OUT [9:0], and (g) represents the serial imaging signal SERIAL_OUT.

As illustrated in (c) of FIG. 7, the counter unit 222*a* outputs the pulse signal CNT5_OUT corresponding to the fifth rise edge of the multiplied CLK. In this case, as illustrated in (d) of FIG. 7, the clock restoring unit 222*b* sets the rise edge of the superimposed signal (High) and, using the rise position of the superimposed signal as a reference, performs resetting at the fifth rise edge of the multiplied CLK (LOW), thereby restoring the reference clock signal CLK with constant pulse widths. As illustrated in (e) of FIG. 7, using the rise of the superimposed signal as a reference, the data restoring unit 222*c* latches the superimposed signal at the timing of the fifth rise edge of the multiplied CLK, thereby restoring the data signal DATA obtained by converting the length of the pulse width to High or Low of the digital signal.

As illustrated in (f) of FIG. 7, the A/D converter 224 performs A/D conversion processing on the imaging signal in synchronization with the rise edges of the reference clock signal CLK, thereby generating the digital imaging signal ADC_OUT [9:0]. Furthermore, as illustrated in (g) of FIG. 7, the P/S converter 225 performs P/S conversion processing on the digital imaging signal ADC_OUT [9:0], on which the A/D converter 224 has performed the A/D conversion processing, in synchronization with the rise edges of the reference clock signal CLK, thereby generating the imaging signal SERIAL_OUT that is serial data.

According to the first embodiment of the disclosure, the PLL unit 221 generates the multiplied CLK whose frequency is higher than that of the superimposed signal and that is for driving the P/S converter 225 in synchronization with any one of the rise edge and the falling edge of the superimposed signal, thereby enabling both an increase in the rate of transmission of the imaging signal and a decrease in the diameter of the distal end part 101.

According to the first embodiment of the disclosure, the restoring unit 222 restores the reference clock signal CLK and the data signal DATA from the superimposed signal whose frequency of any one of the rise edge and the falling edge is stable. For this reason, it is possible to reduce the size of the circuit compared to a different PLL circuit for restoring a reference clock signal from a signal encoded by 8b10b conversion, or the like.

According to the first embodiment of the disclosure, it is not required to additionally arrange a PLL circuit used for only the P/S converter 225 and thus it is possible to reduce the size of the imaging unit 20 and reduce the number of signal lines of the transmission cable 3.

According to the first embodiment of the disclosure, the imaging unit 20 is arranged in parallel with the opening face 101A of the distal end part 101 of the endoscope 2 and thus it is possible to reduce the rigid length of the distal end part 101 of the endoscope 2 and reduce the size of the imaging unit and thus prevent an increase in the diameter.

According to the first embodiment of the disclosure, the superimposed signal generating unit 51 generates, as the superimposed signal, the signal obtained by converting High and Low of the data signal DATA to the length of the pulse length of the reference clock signal CLK and outputs the superimposed signal to the transmission cable 3, which accordingly makes it possible to transmit the data signal DATA and the reference clock signal CLK via the single signal line 33 and thus reduce the diameter of the insertion portion 100 of the endoscope 2.

According to the first embodiment of the disclosure, the first chip 21 is superimposed onto the second chip 22 and therefore, even when the size of the imaging unit 20 is controlled according to the size of the second chip in the case where the number of pixels of the pixel section 211 is reduced, it is possible to implement the PLL unit 221 using a single chip and thus reduce the diameter of the insertion portion 100.

Second Embodiment

A second embodiment of the disclosure will be described. In the first embodiment, the superimposed signal generating unit 51 generates, as the superimposed signal, the signal obtained by converting the rise edge and the falling edge of the data signal DATA that is input from the synchronization signal generating unit 63 to the length of the pulse width of the reference clock signal. In the second embodiment, a signal obtained by associating High or Low of the data signal with transition of the length of the pulse width is transmitted as the superimposed signal. For this reason, a method of generating a superimposed signal by a superimposed signal generating unit according to the second embodiment will be described below. The same configuration as that of the endoscope system 1 according to the above-described first embodiment is assigned with the same reference numbers and letters and description thereof is thus omitted.

Conventional Horizontal Synchronization Signal

Figure 8:
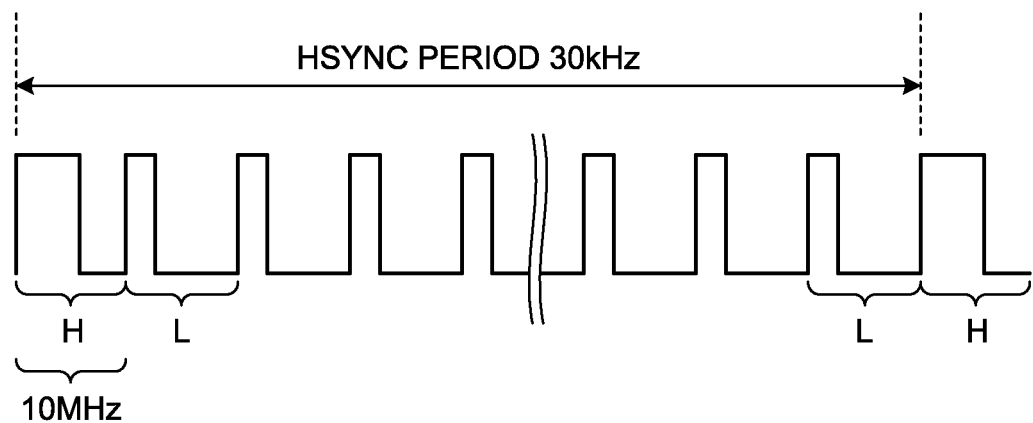
FIG. 8 is a diagram illustrating an exemplary conventional horizontal synchronization signal.
Figure 9:
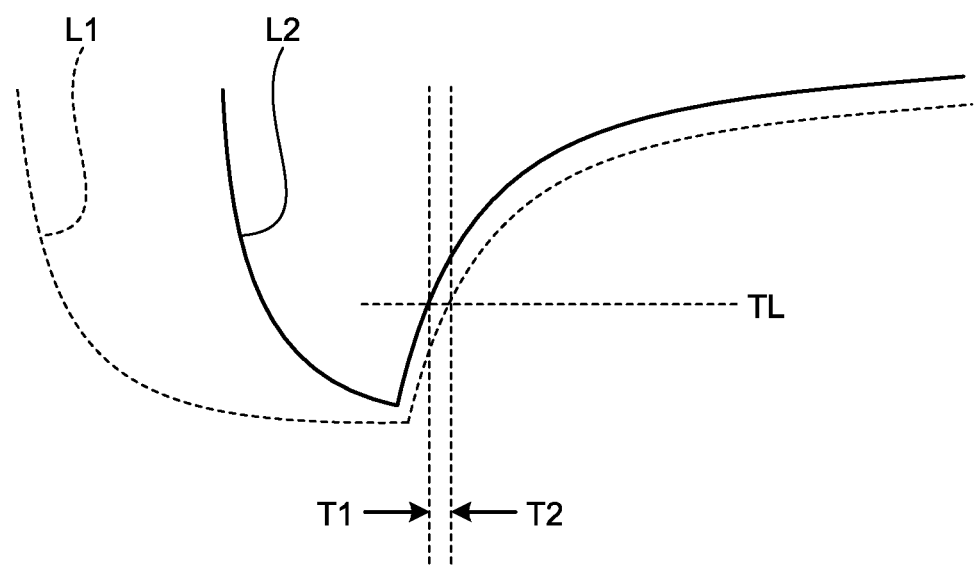
FIG. 9 is a diagram illustrating an exemplary waveform after transmission of the conventional horizontal synchronization signal via a transmission cable.

First of all, a waveform obtained after a horizontal synchronization signal with a modulated pulse width is transmitted via the conventional transmission cable 3 will be described. FIG. 8 is a diagram illustrating an exemplary conventional horizontal synchronization signal. FIG. 9 is a diagram illustrating an exemplary waveform obtained after the conventional horizontal synchronization signal is transmitted via the transmission cable 3. The horizontal synchronization signal in FIG. 8 will be described as a signal in which the period is 30 kHz and High is transmitted per period. A curve L1 represents a waveform obtained after a horizontal synchronization signal whose pulse width is short is transmitted previously and a curve L2 represents a waveform obtained after a horizontal synchronization signal whose pulse width is long is transmitted previously.

As represented by the curve L1 and the curve L2 in FIG. 8 and FIG. 9, in the conventional technique, a horizontal synchronization signal (HSYNC: period of 30 kHz) with a modulated pulse width is transmitted via the transmission cable 3 and, when the transmitted horizontal synchronization signal is not statically determinate completely, timing T1 and timing T2 at which the rise edge of the horizontal synchronization signal, which is transmitted via the transmission cable 3, exceeds a threshold voltage TL according to the pulse width that is transmitted previously mismatch. For this reason, in the conventional technique, a jitter occurs in the superimposed signal that is input to the PLL unit 221 according to the transmitted data pattern. Specifically, as represented by the curve L1 and the curve L2 in FIG. 9, when superimposed signals each with a long pulse width and superimposed signals each with a short pulse width are transmitted alternately via the transmission cable 3, the timings at each of which the rise edge of the superimposed signal exceeds the threshold voltage TL of the PLL unit 221 alternately come first and behind, which results in a jitter. The period of the jitter corresponds to the transmitted data pattern and, as illustrated in FIG. 8, is 30 kHz when the horizontal synchronization signal is transmitted. As a result, the jitter in the output signal of the PLL unit 221 deteriorates because of the jitter resulting from the switch between the long pulse width and the short pulse width via the transmission cable 3.

Figure 10:
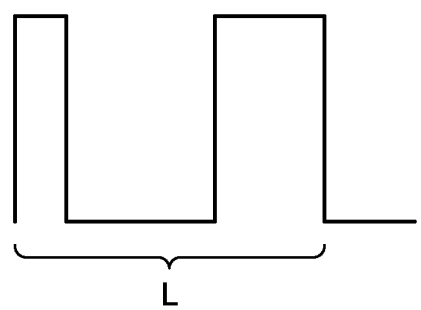
FIG. 10 is a diagram illustrating an exemplary definition of a data signal that is transmitted by a superimposed signal generating unit according to a second embodiment of the disclosure.
Figure 11:
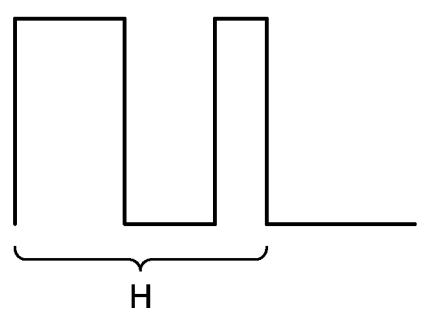
FIG. 11 is a diagram illustrating an exemplary definition of a data signal that is transmitted by the superimposed signal generating unit according to the second embodiment of the disclosure.
Figure 12:
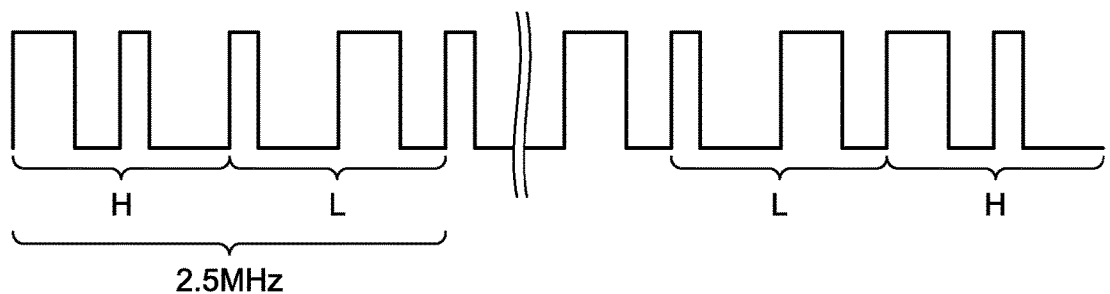
FIG. 12 is a diagram illustrating an exemplary definition of a data signal that is transmitted by the superimposed signal generating unit according to the second embodiment of the disclosure.

Under the circumstances, the superimposed signal generating unit 51 transmits the data signal DATA whose High and Low are associated with transition of the length of the pulse width. Specifically, as illustrated in FIG. 10 and FIG. 11, the superimposed signal generating unit 51 defines a pattern in which a long pulse width comes after a short pulse width as "L" (Low) and defines a pattern in which a short pulse width comes after a long pulse width as "H" (High). As illustrated in FIG. 12, the superimposed signal generating unit 51 transmits the data signal DATA whose High and Low are associated with transition of the length of the pulse width via the transmission cable 3 and therefore the period during which the same pulse width is transmitted correspond to two clocks at maximum. As a result, longness and shortness of the pulse width switches frequently and accordingly the frequency band of the jitter resulting from switch of the pulse width increases (for example, 2.5 MHz when High and Low of the data signal DATA are transmitted alternately) and less effect is on the PLL unit 221.

Figure 13:
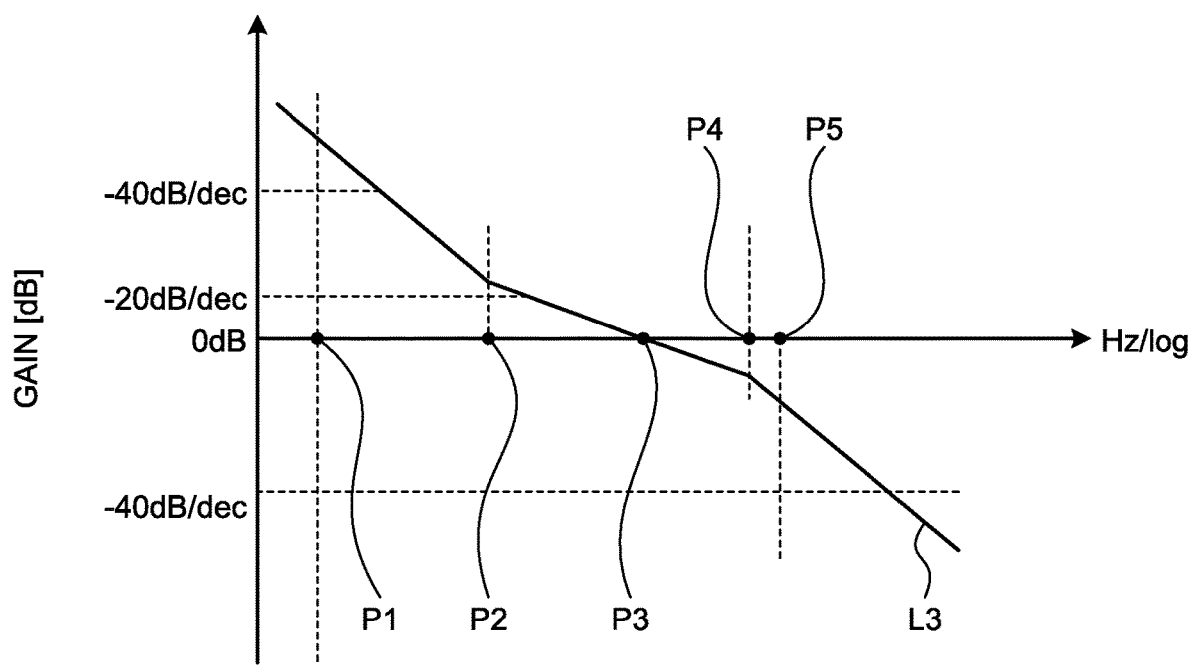
FIG. 13 is a diagram illustrating frequency characteristics of an open loop gain of a PLL unit according to the second embodiment of the disclosure.

FIG. 13 is a diagram illustrating frequency characteristics of an open loop gain of the PLL unit 221. In FIG. 13, the vertical axis represents the gain [dB] and the horizontal axis represents the frequency Hz/log. In FIG. 13, a polygonal line L3 represents the frequency characteristics of the PLL unit 221. A point P1 represents the frequency of 30 kHz of the conventional horizontal synchronization signal, and a point P2 represents 189 kHz, a point P3 represents 700 kHz, a point P4 represents 2.0 MHz and a point P5 represents 5 MHz.

As represented by the points P1 to P5, the jitter is attenuated as the frequency increases and thus, when the frequency of the jitter is high, less effect is on the PLL unit 221. As a result, even when the data signal DATA is transmitted with its High and Low being associated with transition of the length of the pulse width, it is possible to reduce deterioration of the jitter in the output signal of the PLL unit 221.

According to the second embodiment of the disclosure described above, the superimposed signal generating unit 51 generates, as a superimposed signal, a signal obtained by associating High and Low of the data signal DATA with transition of the length of the pulse width of the reference clock signal CLK and outputs the superimposed signal to the transmission cable 3 and this makes it possible to achieve the same effect as that of the above-described first embodiment and reduce deterioration of the jitter of the output signal of the PLL unit 221.

Other Embodiments

Various embodiments can be formed by combining multiple components disclosed in the above-described first and second embodiments of the disclosure. For example, some of all the components described in the first and second embodiments of the disclosure described above may be omitted. The components described in the first and second embodiments of the disclosure described above may be combined as appropriate.

In the first and second embodiments of the disclosure, the reference clock signal generating unit 64 and the synchronization signal generating unit 63 are arranged in the processor 6. Alternatively, they may be arranged in the connector 5 of the endoscope 2. Needless to say, the superimposed signal generating unit 51 may be arranged in the processor 6.

In the first and second embodiments of the disclosure, the controller and the light source device are independent from each other. Alternatively, they may be formed integrally.

In the first and second embodiments of the disclosure, the "units" may be read also as "circuits", etc. For example, the control unit may be also read as "control circuit", etc.

The first and second embodiments of the disclosure are about endoscope systems. Alternatively, for example, a capsule endoscope, a video microscope that captures images of a subject, a mobile phone with image capturing function, and a table terminal device with the image capturing function may be used as well.

The disclosure achieves an effect that the rate of transmission of an imaging signal increases and the diameter of the distal end part reduces.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an imager configured to generate an imaging signal by receiving light and performing photoelectric conversion;
   a transmission path configured to connect a controller configured to perform image processing on the imaging signal that is generated by the imager, and the imager with each other and transmit the imaging signal;
   a superimposed signal generating circuit that is arranged on a side of a proximal end of the transmission path, the superimposed signal generating circuit being configured to generate, as a superimposed signal, a signal obtained by associating High and Low of a pulsed data signal that is input from an outside of the endoscope with a change in a pulse width of a pulsed reference clock signal that is input from an outside of the endoscope and output the superimposed signal to the transmission path;
   a parallel-serial converter circuit that is arranged on a side of a distal end of the transmission path, the parallel-serial converter circuit being configured to perform parallel-serial conversion on the imaging signal and output the converted imaging signal to the transmission path;
   a PLL circuit that is arranged on the side of the distal end of the transmission path, the PLL circuit being configured to generate a multiplied clock signal that is obtained by multiplying a frequency of the superimposed signal by at least 2 in synchronization with any one of a rise edge and a falling edge of the superimposed signal, the PLL circuit being configured to output the generated multiplied clock signal directly to both the parallel-serial converter circuit and a restoring circuit, the multiplied clock signal being a signal for driving the parallel-serial converter circuit;
   the restoring circuit that is arranged on the side of the distal end of the transmission path, the restoring circuit being configured to restore, based on the superimposed signal and the multiplied clock signal, the reference clock signal and the data signal contained in the superimposed signal; and
   a timing generating circuit that is arranged on the side of the distal end of the transmission path, the timing generating circuit being configured to generate, based on the reference clock signal and the data signal, a drive signal for driving the imager.

2. The endoscope according to claim 1,
   wherein the superimposed signal generating circuit is configured to generate, as the superimposed signal, a signal obtained by converting High and Low of the data signal to a length of the pulse width of the reference clock signal.

3. The endoscope according to claim 1,
   wherein the superimposed signal generating circuit is configured to generate, as the superimposed signal, a signal obtained by associating High and Low of the data signal with transition of a length of the pulse width of the reference clock signal.

4. The endoscope according to claim 1, wherein the restoring circuit includes
   a clock restoring circuit configured to generate the reference clock signal having a constant pulse width, based on the superimposed signal and the multiplied clock signal; and
   a data restoring circuit configured to restore, based on the superimposed signal and the multiplied clock signal, a length of a pulse width of the superimposed signal into High or Low of the data signal.

5. The endoscope according to claim 1, wherein the imager includes
   a first chip on which at least a pixel section configured to generate the imaging signal is formed; and
   a second chip on which at least the parallel-serial converter circuit, the PLL circuit, and the restoring circuit are formed, and
   the first chip is superimposed on the second chip.

6. The endoscope according to claim 1, wherein the imager is arranged in parallel with an opening face of a distal end part of an insertion portion to be inserted into a subject.

7. The endoscope according to claim 1, further comprising:
   an insertion portion to be inserted into a subject; and
   a connector that is detachably connected to the controller,
   wherein the insertion portion includes the imager, the parallel-serial converter circuit, the PLL circuit, and the restoring circuit, and
   the connector includes the superimposed signal generating circuit.

8. The endoscope according to claim 1, wherein the restoring circuit is configured to restore a reference clock signal having a constant pulse width by setting a rise edge of the superimposed signal and, using a rise position of the superimposed signal as a reference, performing resetting at an edge of a multiplied CLK, which is the edge counted by a given number.

9. An endoscope system comprising:
   an endoscope including an imager configured to generate an imaging signal by receiving light and performing photoelectric conversion;
   a controller configured to perform image processing on the imaging signal that is generated by the imager;
   a transmission path configured to connect the imager and the controller with each other and transmit the imaging signal;
   a data signal generating circuit configured to generate a pulsed data signal and output the pulsed data signal;
   a reference clock signal generating circuit configured to generate a pulsed reference clock signal and output the pulsed reference clock signal;
   a superimposed signal generating circuit that is arranged on a side of a proximal end of the transmission path, the superimposed signal generating circuit being configured to generate, as a superimposed signal, a signal obtained by associating High and Low of the data signal with a change in a pulse width of the reference clock signal and output the superimposed signal to the transmission path;
   a parallel-serial converter circuit that is arranged on a side of a distal end of the transmission path, the parallel-serial converter circuit being configured to perform parallel-serial conversion on the imaging signal and then output the converted imaging signal to the transmission path;

a PLL circuit that is arranged on the side of the distal end of the transmission path, the PLL circuit being configured to generate a multiplied clock signal that is obtained by multiplying a frequency of the superimposed signal by at least 2 in synchronization with any one of a rise edge and a falling edge of the superimposed signal, the PLL circuit being configured to output the generated multiplied clock signal directly to both the parallel-serial converter circuit and a restoring circuit, the multiplied clock signal being a signal for driving the parallel-serial converter circuit;

the restoring circuit that is arranged on the side of the distal end of the transmission path, the restoring circuit being configured to restore, based on the superimposed signal and the multiplied clock signal, the reference clock signal and the data signal contained in the superimposed signal; and a timing generating circuit that is arranged on the side of the distal end of the transmission path, the timing generating circuit being configured to generate, based on the reference clock signal and the data signal, a drive signal for driving the imager.

* * * * *